United States Patent [19]

Mueller et al.

[11] Patent Number: 4,728,435
[45] Date of Patent: Mar. 1, 1988

[54] DECOLORIZATION OF AQUEOUS GLYOXAL SOLUTIONS

[75] Inventors: Guenther Mueller, Ludwigshafen; Rolf Ramsteiner, Neuhofen; Fritz Graf, Speyer; Leopold Hupfer, Friedelsheim, all of Fed. Rep. of Germany

[73] Assignee: BASF Aktiengesellschaft, Ludwigshafen, Fed. Rep. of Germany

[21] Appl. No.: 915,723

[22] Filed: Oct. 6, 1986

[30] Foreign Application Priority Data

Oct. 11, 1985 [DE] Fed. Rep. of Germany ....... 3536263

[51] Int. Cl.$^4$ .............................................. B01D 15/00
[52] U.S. Cl. .................................... 210/670; 210/694; 210/917; 568/492
[58] Field of Search ..................... 210/670, 694, 917; 502/25, 27; 568/492

[56] References Cited

U.S. PATENT DOCUMENTS

| 1,189,896 | 7/1916 | Wijnberg | 502/25 |
| 1,709,284 | 4/1929 | Sauer et al. | 502/25 |
| 3,270,062 | 8/1966 | Merz et al. | 260/601 R |
| 3,507,764 | 4/1970 | Asahi et al. | 204/180 |
| 3,574,765 | 4/1971 | Kuryla et al. | 568/492 |
| 3,860,656 | 1/1975 | McCain, Jr. et al. | 260/601 R |
| 4,521,632 | 6/1985 | Wickenhaeuser et al. | 568/492 |

FOREIGN PATENT DOCUMENTS 3402733 11/1984 Fed. Rep. of Germany .

*Primary Examiner*—Ivars Cintins
*Attorney, Agent, or Firm*—John H. Shurtleff

[57] ABSTRACT

An aqueous glyoxal solution is decolorized by a process in which the said solution is passed over granulated active carbon which is arranged in a fixed bed and whose differential pore radius distribution has a maximum of from 10 to 100 Å, the Peclet number being from 500 to 5000, the decolorized glyoxal solution is discharged, the active carbon bed is then regenerated by treating it with an aqueous solution of an alkaline agent and then with an aqueous acid, and further glyoxal solution to be decolorized is passed over the active carbon regenerated in this manner.

14 Claims, No Drawings

DECOLORIZATION OF AQUEOUS GLYOXAL SOLUTIONS

Glyoxal is available commercially as an aqueous solution of about 40% strength by weight. These glyoxal solutions are used, for example, for the production of textile and paper auxiliaries or for the preparation of disinfectants and must have a color number of $\leq 10$ APHA.

Glyoxal is prepared industrially by oxidizing acetaldehyde with nitric acid or by the oxidative dehydrogenation of ethylene glycol over special catalysts. In both cases, the crude aqueous glyoxal solutions obtained contain acids as byproducts and have a more or less pronounced yellow color.

There has therefore been no lack of attempts to purify and decolorize these crude glyoxal solutions. According to U.S. Pat. No. 3,270,062 or German Laid-Open Application DOS No. 3,402,733, byproducts, such as acetic acid, formic acid and glycolic acid, are removed by treating the crude solutions with fixed-bed anion exchangers or with solutions of tertiary amines. In these processes, some of the components responsible for the yellow coloration, which have not been identified chemically, are retained. However, since the yellow coloration breaks through well before the acid absorption capacity of the anion exchanger is exhausted, it is impossible to prepare glyoxal solutions having a color number of $\leq 10$ APHA in an economical manner. Removal of acids is therefore usually followed by decolorization of the glyoxal solution with powdered active carbon, which is kept in suspension mechanically by circulating the solution or by thorough stirring and is separated off again after several hours by filtration (U.S. Pat. Nos. 3,860,656 and 3,507,764).

The disadvantage of the batchwise procedure described was overcome by using granulated active carbon arranged in adsorption towers. However, experience has shown that the specific decolorization capacity of the active carbon depends to a very great extent on the particle size and consumption of active carbon increases 10-fold in the case of the granulated material.

We have found that an aqueous glyoxal solution can be decolorized in a substantially more advantageous manner if the said solution is passed over granulated active carbon which is arranged in a fixed bed and whose differential pore radius distribution has a maximum of from 10 to 100 A, the Peclet number being from 500 to 5000, the decolorized glyoxal solution is discharged, the active carbon bed is then regenerated by treating it with an aqueous solution of an alkaline agent and then with an aqueous acid, and further glyoxal solution to be decolorized is passed over the active carbon regenerated in this manner.

The novel process is useful for decolorizing the 10–60% strength by weight aqueous glyoxal solutions which are obtainable, for example, in the industrial synthesis and which usually have color numbers of from 50° to 200° APHA.

The active carbon used is a granulated active carbon which has a particle size of, for example, from 0.5 to 2.5 mm, preferably from 0.9 to 1.3 mm, and whose differential pore radius distribution has a maximum of from 10 to 100 A, preferably from 20 to 50 A, the Peclet number being from 500 to 5000, preferably from 1500 to 3000. The differential pore radius distribution is defined in VDI Guideline 3,674. The Peclet number is the ratio of the flow of material to the diffusion flow over the active carbon (cf. Kennzahlen der Verfahrenstechnik, Hüttig-Verlag, Heidelberg, 1985, page 60).

The glyoxal solution is passed over the active carbon bed at up to 60° C., preferably from 10° to 50° C. The minimum treatment time is about one hour. When the decolorized glyoxal solution has been discharged, the active carbon is regenerated by treating it with an aqueous solution of an alkaline agent. Advantageously used alkaline agents are strong alkalis, such as KOH or NaOH. From 0.2 to 10% strength sodium hydroxide solution or potassium hydroxide solution is preferably used. After the treatment with the alkaline solution, the active carbon is washed with a dilute aqueous acid. Examples of suitable acids are sulfuric acid, phosphoric acid, formic acid and nitric acid. A 0.5–15% strength nitric acid is preferably used. The regeneration is carried out at up to 90 C., advantageously at room temperature.

Using the novel process, aqueous glyoxal solutions can be decolorized in a particularly advantageous manner. The fact that granulated active carbon with the particular differential pore distribution and at the stated Peclet numbers has the high decolorization capacity observed here and can be regenerated in such a simple manner with recovery of the initial decolorization capacity is very surprising.

The decolorization according to the invention can be carried out by a continuous procedure and is advantageously effected in an adsorption tower in which the active carbon is arranged as a fixed bed. However, it is also possible to use other conventional apparatuses in which the glyoxal solution can be brought into contact with the active carbon.

EXAMPLE 1 liter of dry granulated active carbon (sieve fraction 0.1–0.3 mm) having a maximum of 20 A in the differential pore distribution is introduced into an adsorption tower having a diameter of 4 cm and a length of 100 cm. Thereafter, the adsorption tower is evacuated by means of a water pump, and is slowly filled from below with an aqueous 40% strength glyoxal solution having a color number of 57 APHA.

The glyoxal solution is pumped continuously at room temperature through the adsorption tower at a flow rate of 0.9 m/h. Under these conditions, the Peclet number is 1500. The glyoxal solution whose color number has been reduced to $\leq 10$ APHA is obtained during a life of 50 hours.

To effect regeneration, the glyoxal solution is discharged and the active carbon tower is then flushed with compressed air and washed glyoxal-free with water. The active carbon bed is then treated at room temperature with 0.5% strength by weight sodium hydroxide solution, which is passed through from above at a flow rate of 0.5 m/h. About 10 bed volumes of dilute sodium hydroxide solution are required. The active carbon is then washed with 1% strength by weight nitric acid until the discharge has a pH of less than 4.

The adsorption tower is now refilled with the glyoxal solution to be decolorized and the procedure described above is carried out. Even after 10 regenerations, no fall in the decolorization capacity was observed.

We claim:

1. A process for decolorizing an aqueous glyoxal solution which process comprises:

passing said solution over a granulated active carbon which is arranged in a fixed bed and which has a maximum differential pore radius distribution of from 10 to 100 A, the Peclet number being from 500 to 5000, discharging the decolorized glyoxal solution from said bed, then regenerating the active carbon bed at a temperature up to 90° C. by first treating it with an aqueous solution of an alkaline agent and then with an aqueous acid, and again passing further glyoxal solution to be decolorized over the active carbon bed regenerated in this manner.

2. A process as claimed in claim 1, wherein a 10-60% strength by weight aqueous glyoxal solution is decolorized.

3. A process as claimed in claim 1, wherein a 0.2-10% strength by weight sodium hydroxide solution or potassium hydroxide solution is used as the aqueous solution of an alkaline agent for the regeneration.

4. A process as claimed in claim 1, wherein a 0.5-15% strength by weight nitric acid is used as the aqueous acid for the regeneration.

5. A process as claimed in claim 1, wherein, the regeneration steps are carried out at about room temperature.

6. A process as claimed in claim 1, wherein the granulated active carbon has a particle size of from 0.5 to 2.5 mm.

7. A process as claimed in claim 1, wherein the granulated active carbon has a maximum differential pore radius distribution of 20 to 50 A and a Peclet number of from 1500 to 3000.

8. A process as claimed in claim 7, wherein the granulated active carbon has a particle size of from 0.9 to 1.3 mm.

9. A process as claimed in claim 8, wherein the regeneration steps are carried out at about room temperature.

10. A process as claimed in claim 7, wherein the regeneration steps are carried out at about room temperature.

11. A process as claimed in claim 1, wherein a 10-60% strength glyoxal solution is continuously decolorized to a color number equal to or less than 10 APHA, and the granulated active carbon is regenerated before the color number exceeds this value of 10 APHA.

12. A process as claimed in claim 11, wherein the regeneration steps are carried out at about room temperature.

13. A process as claimed in claim 12, wherein the granulated active carbon has a particle size of from 0.5 to 2.5 mm., a maximum differential pore radius of 20 to 50 A and a Peclet number of from 1500 to 3000.

14. A process as claimed in claim 13, wherein the aqueous solution of an alkylating agent is a 0.2-10% strength by weight sodium or potassium hydroxide solution, and the aqueous acid is a 0.5-15% by weight nitric acid.

* * * * *